(12) United States Patent
Pandey et al.

(10) Patent No.: US 7,043,961 B2
(45) Date of Patent: May 16, 2006

(54) TOOL CALIBRATOR AND TRACKER SYSTEM

(75) Inventors: Rajesh Pandey, Plantation, FL (US); Louis Arata, Mentor, OH (US); Brandon Larocque, Hollywood, FL (US)

(73) Assignee: Z-Kat, Inc., Hollywood, FL (US)

( * ) Notice: Subject to any disclaimer, the term of this patent is extended or adjusted under 35 U.S.C. 154(b) by 0 days.

(21) Appl. No.: 10/062,842

(22) Filed: Jan. 30, 2002

(65) Prior Publication Data

US 2003/0209096 A1 Nov. 13, 2003

Related U.S. Application Data

(60) Provisional application No. 60/265,483, filed on Jan. 30, 2001.

(51) Int. Cl.
*G01B 18/00* (2006.01)
*A61B 1/00* (2006.01)

(52) U.S. Cl. .................. 73/1.81; 73/1.75; 73/1.79; 73/1.88

(58) Field of Classification Search .............. 73/1.75, 73/1.78, 1.79, 1.81, 1.88; 600/117, 424
See application file for complete search history.

(56) References Cited

U.S. PATENT DOCUMENTS

| | | | | |
|---|---|---|---|---|
| 5,517,990 A | * | 5/1996 | Kalfas et al. ............... | 600/414 |
| 5,552,822 A | * | 9/1996 | Nallakrishnan ............ | 348/79 |
| 5,921,992 A | * | 7/1999 | Costales et al. ............ | 606/130 |
| 5,954,648 A | * | 9/1999 | Van Der Brug ............ | 600/411 |
| 5,987,960 A | * | 11/1999 | Messner et al. ............ | 73/1.79 |
| 6,081,336 A | * | 6/2000 | Messner et al. ........... | 356/624 |
| 6,112,113 A | * | 8/2000 | Van Der Brug et al. ... | 600/427 |
| 6,187,018 B1 | * | 2/2001 | Sanjay-Gopal et al. .... | 606/130 |
| 6,235,038 B1 | * | 5/2001 | Hunter et al. .............. | 606/130 |
| 6,236,875 B1 | * | 5/2001 | Bucholz et al. ............ | 600/407 |
| 6,306,126 B1 | * | 10/2001 | Moctezuma .................. | 606/1 |
| 6,347,460 B1 | * | 2/2002 | Forrer et al. ................. | 33/626 |
| 6,377,839 B1 | * | 4/2002 | Kalfas et al. ............... | 600/426 |
| 6,402,762 B1 | * | 6/2002 | Hunter et al. .............. | 606/130 |
| 6,434,847 B1 | * | 8/2002 | Duckett et al. ............. | 33/520 |
| 6,497,134 B1 | * | 12/2002 | Faul et al. .................. | 73/1.81 |
| 6,511,418 B1 | * | 1/2003 | Shahidi et al. ............ | 600/117 |
| 6,517,478 B1 | * | 2/2003 | Khadem ..................... | 600/117 |
| 6,584,339 B1 | * | 6/2003 | Galloway et al. .......... | 600/426 |

\* cited by examiner

*Primary Examiner*—Hezron Williams
*Assistant Examiner*—David A. Rogers
(74) *Attorney, Agent, or Firm*—Fay, Sharpe, Fagan, Minnich & McKee, LLP

(57) ABSTRACT

A standard medical or surgical tool's axis is located by attaching to the tool a plurality of a location indicating elements or markers having a known geometric or spatial relationship, and placing the tool in a tool calibrator that supports the tool in a manner that allows tools of different diameters to be rotated while maintaining the tool's axis in a fixed or stable orientation. As the tool is rotated, a marker locating system tracks the positions of the markers on the tool and then extrapolates or determines the axis of rotation with respect to the markers clamped to the tool. The tool calibrator has a second set of position indicating elements or markers with fixed geometric or spatial relationship with one another and with respect to a stop, against which the end or tip of the tool is placed.

16 Claims, 4 Drawing Sheets

TOOL CALIBRATOR AND TRACKER SYSTEM

RELATED APPLICATION

This application claims priority to U.S. Provisional Application No. 60/265,483 filed Jan. 30, 2001 entitled, "Tool Calibrator and Tracker System".

TECHNICAL FIELD OF THE INVENTION

This invention relates generally to a tool calibrator for a medical tool tracking system.

BACKGROUND OF THE INVENTION

Three-dimensional diagnostic images of the brain, spinal cord, and other body portions can be produced by diagnostic imaging equipment such as CT scanners, magnetic resonance imagers, three-dimensional fluoroscopes, and the like. These imaging modalities often provide structural detail with a resolution of a millimeter or better. Image guided interventional systems have been developed to utilize this data to assist a doctor, surgeon or other specialist in connection with planning of an medical, surgical or other type of interventional procedure and in accurately locating a region of interest within the body of a patient during the procedure.

Image guided interventional systems may also be used to display position and orientation of a medical tool with respect to the images of the patient during a interventional procedure. Multiple views of patient image data are typically displayed on a monitor visible to the person handling the tool during a medical or medical procedure. These views may include axial, sagittal, and coronal views of the patient. A fourth oblique view is sometimes displayed, presenting image data in a plane orthogonal to a tip of the tool. The location of the tip of the tool, the tool's trajectory, and diameter of the tool head are displayed on one or more of these images. The algebraic distance between the tip of the tool and a desired position may also be displayed numerically on the monitor.

Given the nature of image guided procedures, it is necessary to be able to track the location of the tip of the tool, the tool's trajectory, and diameter of the tool head with a high degree of precision, often requiring calibration to less than a millimeter in accuracy. The position and orientation of tools are tracked by use of a tracking system. The tracking system tracks the tools by detecting the position of three or more markers that have a known geometric relationship with respect to each other and to the tool. The tracking system may utilize any type of tracking technique, for example optical, magnetic, radio frequency, and fiber-optic, to name a few. The markers can be, depending on the type of system, passive or active. One well known example of a tracking system uses as markers spheres that reflect infrared energy. The tracking systems baths the spheres in infrared radiation. Multiple, spatially separated cameras are used detect the relative positions of the spheres.

The position indicating elements, or markers, are positioned in a unique pattern for each tool in order to allow the tracking system to be able to distinguish one tool from another. In other words, the unique pattern can be said to characterize the tool. The tracking system is preprogrammed with information related to where the tip and trajectory of each tool is with respect to the tool's position indicating elements and with information related to the diameter of the tool head. For instance, with respect to a tracked probe having three infrared emitters, the tracking system maintains information related to where the tip of the probe is with relationship to a selected point on a plane defined by the three infrared emitters. Based on this information, a precise location of the tip can be calculated and displayed on one of the monitors.

In a variety of medical tools such as drills, probes, endoscopes, etc., it is often beneficial to a doctor, surgeon or other individual to make changes to the tool which may affect the positioning of the tip as well as the diameter of the tool head. For instance, on a medical drill it is often helpful for the surgeon to be able to change the size and length of a drill bit to perform different medical procedures. Further, with respect to the probes, it is often desirous to replace different length and diameter shafts on the probe handle in order to reach different regions in the patient.

Unfortunately, because the position of the tip of each tool with respect to the tool's position indicating elements and the tool head diameter in conventional systems are preprogrammed changes to the tool which affect the location of the tip and diameter of the tool head cannot easily be made. If changes are made, an operator needs to measure the new relationship between the tip of the tool and the tool's position indicating elements and enter this information into the computer. Further, information related to a new diameter of the tool head may also need to be entered. This process is time consuming and cumbersome. If the new information is not entered into the tracking system, the tip of the tool will not be properly tracked and displayed on the monitor.

It is desirable to allow standard surgery tools to be used with image guided intervention systems. This feature would help to keep down the cost of image guided surgeries. Such a tool calibrator is disclosed in U.S. Pat. No. 5,987,960, which is incorporated herein by reference. The tool calibrator includes two movable blocks shaped to slidably engage and secure a tool in a desired position. The tool is secured by a series of staggered V shaped grooves on each of the two movable blocks having a known geometrical relationship with a diameter of a tool head of the tool. The tool calibrator further includes at least one position indicating element for communicating a location of the tool calibrator in an operating room or other area. A position and direction of a tip of the tool is determined by comparing a location of the tool secured within the tool calibrator to the location of each of the two movably blocks. Further, based on the location of each of the two movable blocks, the diameter of the tool head is calculated. The tool calibrator is able to calibrate a location of a tip of a tool, a direction in which the tip is pointing, and a diameter of a tool head all at once. The direction in which the tip of the tool is pointing is determined by comparing a relationship between position indicating elements connected to each of the two movable blocks securing the tool with position indicating elements connected to the tool. The location of the tip of the tool is determined by comparing the location of the position indicating elements connected to the tool calibrator to the location of position indicating elements connected to the tool. The diameter of the tool is determined by virtue of a known geometrical relationship between the V shaped grooves of two movable blocks and the diameter of the tool head.

SUMMARY OF THE INVENTION

In order to simplify and/or make more accurate the process of calibrating a standard medical or surgical tool for use in an image guided interventional system, a standard medical or surgical tool's axis is located by attaching to the tool a plurality location indicating elements or markers having a known geometric relationship, and placing the tool in a tool calibrator that supports the tool in a manner that allows tools of different diameters to be rotated while maintaining the tool's axis in a fixed or stable orientation. As the tool is rotated, a marker locating system tracks the positions of the markers on the tool and then extrapolates or determines the axis of rotation with respect to the markers clamped to the tool. The tool calibrator may further include a second set of position indicating elements or markers with fixed geometric or spatial relationship with one another and with respect to a stop, against which the end or tip of the tool is placed. The marker locating or tracking system determines the orientation and position of the tip of the tool with respect to the markers attached to the tool. Therefore, a range of standard medical tools can be accurately calibrated in a comparatively simple fashion, thus avoiding the need of specially constructed tools.

In one example, a frame of a tool calibrator for supporting a surgical or medical tool or instrument is configured so that it contacts the tool at at least two separate locations along its axis, thereby permitting any tool having a diameter within some defined range of diameters to be supported and rotated with its axis in a stable or fixed location. The tool calibrator may also incorporate an element that holds the tool against the frame as it is being rotated.

In another example, a tool calibrator for an image guided interventional system forms a support frame using a groove, preferably a "V" shaped or similar groove, formed in a surface for receiving the tool and holding in a fixed position its axis as it is rotated. The tool calibrator further includes a tool holder operable to retain the tool in the groove as it is being rotated, and a tool stop operable to retain a tip of the tool in a fixed location with respect to the calibrator. The tool calibrator has a plurality of position indicating elements with fixed spatial relationship with one another and to the tool stop.

DETAILED DESCRIPTION OF THE DRAWINGS

Figure 1:
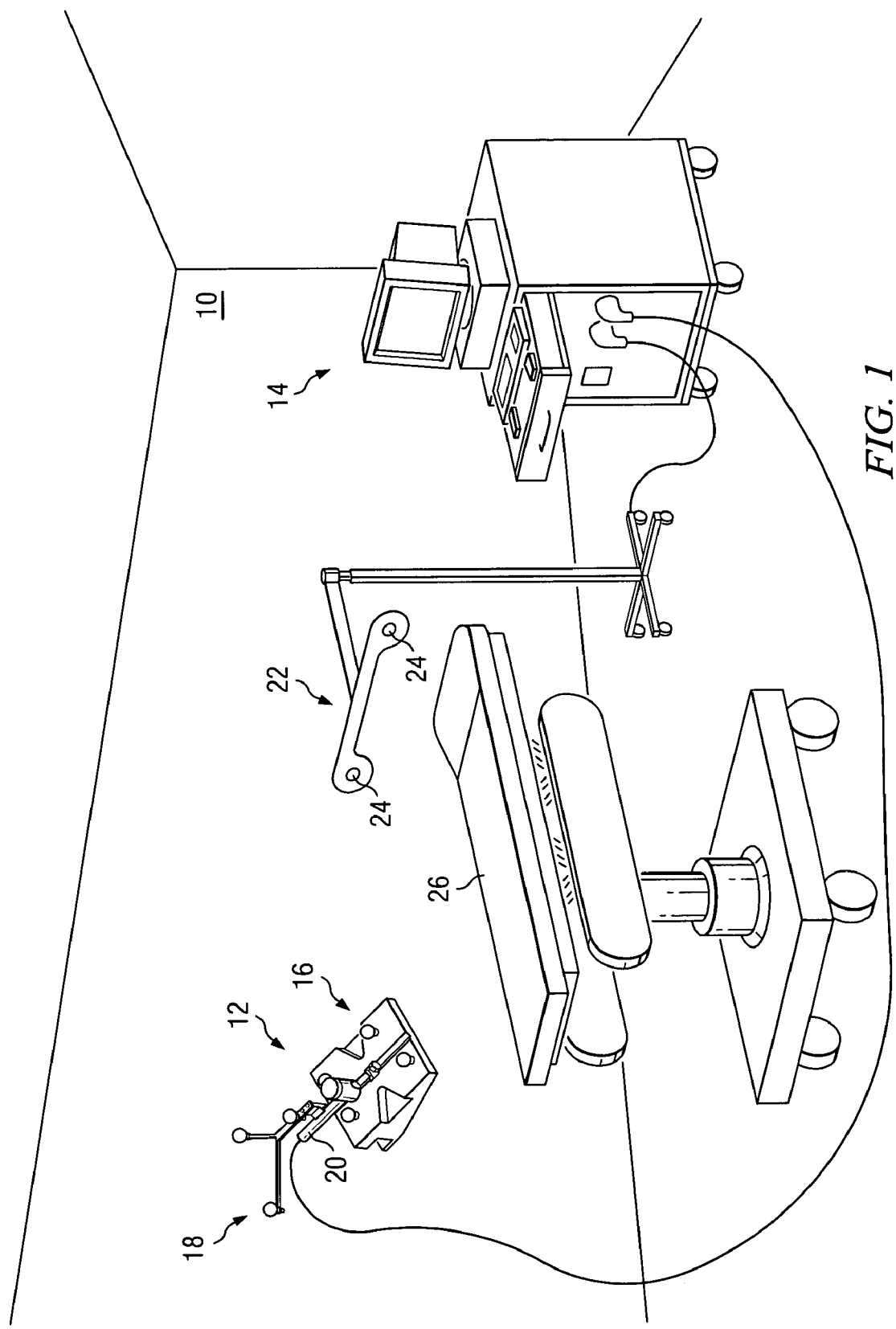
FIG. 1 is a perspective view of a representative example of an operating room in which a tool calibrator and medical or surgical instrument tracking system may be deployed.

FIG. 1 is a perspective view of an operating room 10 in which a tool calibrator and tracker system 12 is deployed and used with an image guided surgery system 14. Tool calibrator and tracker system 12 includes a tool calibrator 16 and a tool tracker 18. Tool tracker 18 is attachable to a tool 20, such as a medical probe, drill or endoscopes. Tool 20 is operable to be installed in tool calibrator 16 to register the tool to the image guided system. A locating system 22 is mounted in a known position relative to an table 26 upon which a patient will be supported. Locating system 22 may be mounted in another manner with respect to another suitable known location in operating room 10. The locating system included, in the illustrative embodiment, is a passive infrared optical system that includes two cameras 24 on an infrared radiation source that illuminates the viewing area of the cameras with infrared radiation. Such systems are well known. However, although the illustrated embodiment may be most advantageously used with a passive infrared tracking system, the invention, in its most general aspects may be utilized with any type of tracking system, including other types of optical systems, RF, magnetic, acoustic or ultrasonic, and fiber optic systems. Furthermore, active position indicating elements or markers, such as, for example, LEDs, may be used in place of the passive ones that are shown in the illustrated embodiment. Power for such elements may be ultrasonic, RF, or magnetic.

As described in more detail below, tool tracker 18 and tool calibrator 16 each includes a plurality of position indicating elements detectable by locating system 22, which are used to provide location and orientation information of tool 20 to image guided surgery system 14.

Figure 2:
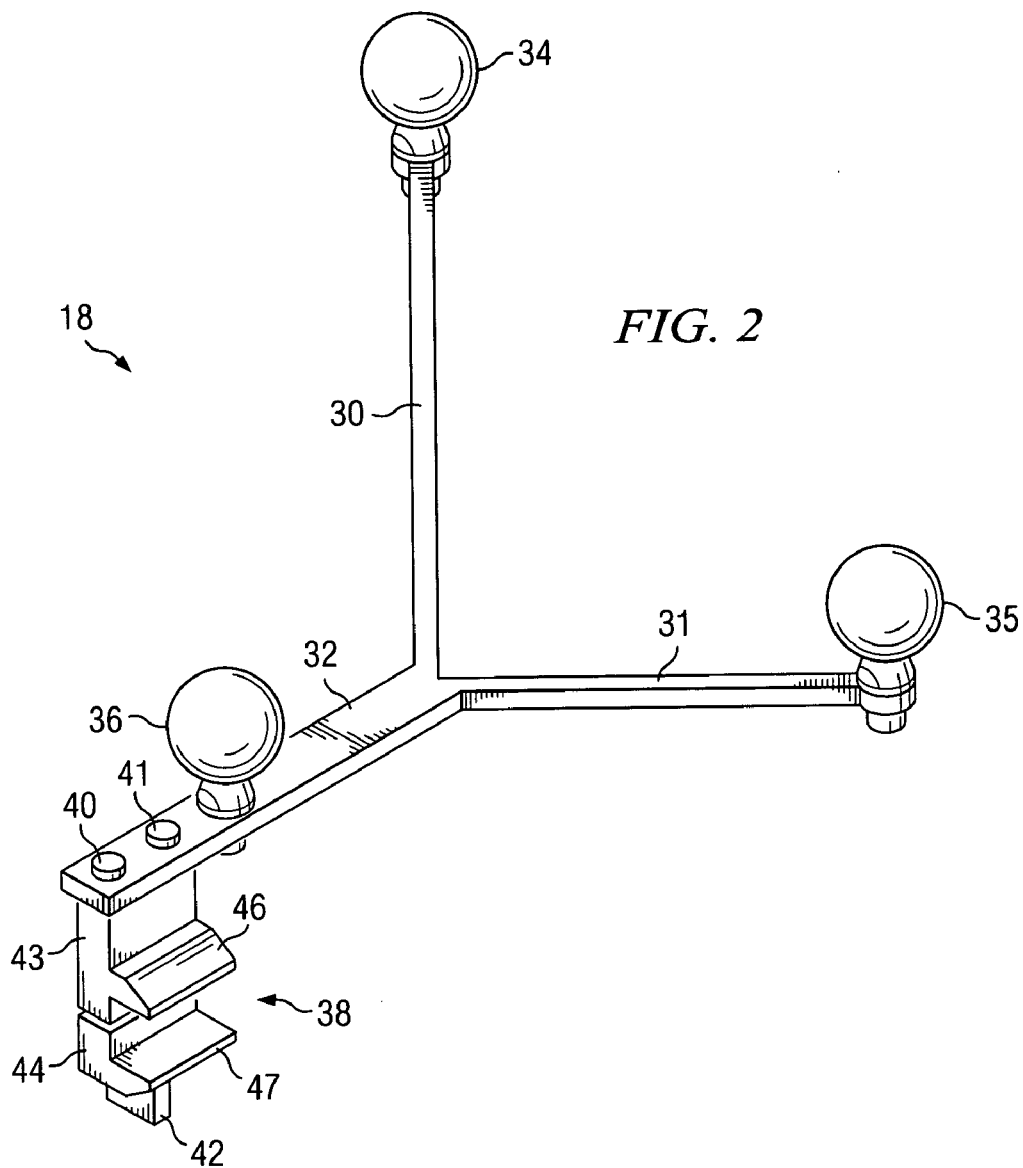
FIG. 2 is a perspective view of an example of a tool tracker.
Figure 3:
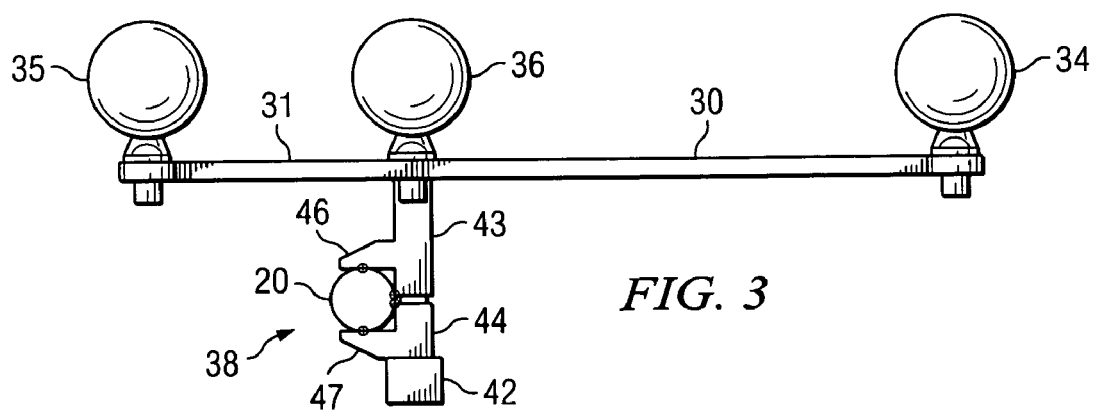
FIG. 3 is an elevational view of the tool tracker.

Referring to FIG. 2 and FIG. 3 for a more detailed perspective view and an elevational view, respectively, of tool tracker 18 of the present invention. Tool tracker 18 provides a detachable tool reference frame that is locatable in space by locating system of image guided surgery system 14. Tool tracker 18 includes a frame that supports at least three positions indicating elements in a fixed and known relationship. A frame having a "Y" shaped configuration as illustrated, will tend to reduce the opportunity of the frame to occlude a position indicating element full view of locating system 22. The frame of the tool tracker includes at least two prong members 30 and 31 coupled to a handle member 32 in a generally Y-shaped configuration. Prong members 30 and 32 may vary from one another in length, and the respective angles they extend from the axis of handle member 32 may be different in shape and length. In the embodiment shown in FIG. 2, prong member 30 is longer than prong member 31. Coupled to generally the distal ends of prong members 30 and 31 are position indicating elements 34 and 35, respectively, which are positioned spaced apart from one another. At least one other position indicating element 36 is coupled to handle member 32, located spaced apart from position indicating elements 34 and 35 and situated in the same plane as devices 34 and 35. Position indicating elements 34 and 35 are in the illustrated embodiment, passive reflectors, but could instead be another type of marker or position indicating element (e.g. active infrared or sonic transmitters), which are detectable by locating system 22.

A medical tool is releasably fastened to tool tracker 18 by means of, for example, a clamp. A clamp offers an advantage that no modification to a medical tool is necessary for fastening the medical tool to the tool tracker. In the illustrated embodiment, clamp 38 secures representative medical tool 20 to tool tracker 18. Fasteners such as screws 40 and 41 may be used to attach clamp 38 to handle member 32. Clamp 28 is preferably a C-shaped clamp with two coordinating parts 43 and 44, which may be tightened around medical tool 20 by a device such as a thumbscrew 42. Coordinating parts 43 and 44 of C-clamp 28 include two opposing fingers 46 and 47 which point slightly toward one another to ensure a secure hold and fixed known position of tool 20 with respect to tool tracker 18 when coordinating parts 43 and 44 are tightened. As shown in FIG. 3, tool 20 is pushed by fingers 46 and 47 toward the back surfaces of clamp 38, and engages the corners of both coordinating parts 43 and 44 of clamp 38. This ensures a solid four-point contact between tool tracker 18 and tool 20.

Figure 4:
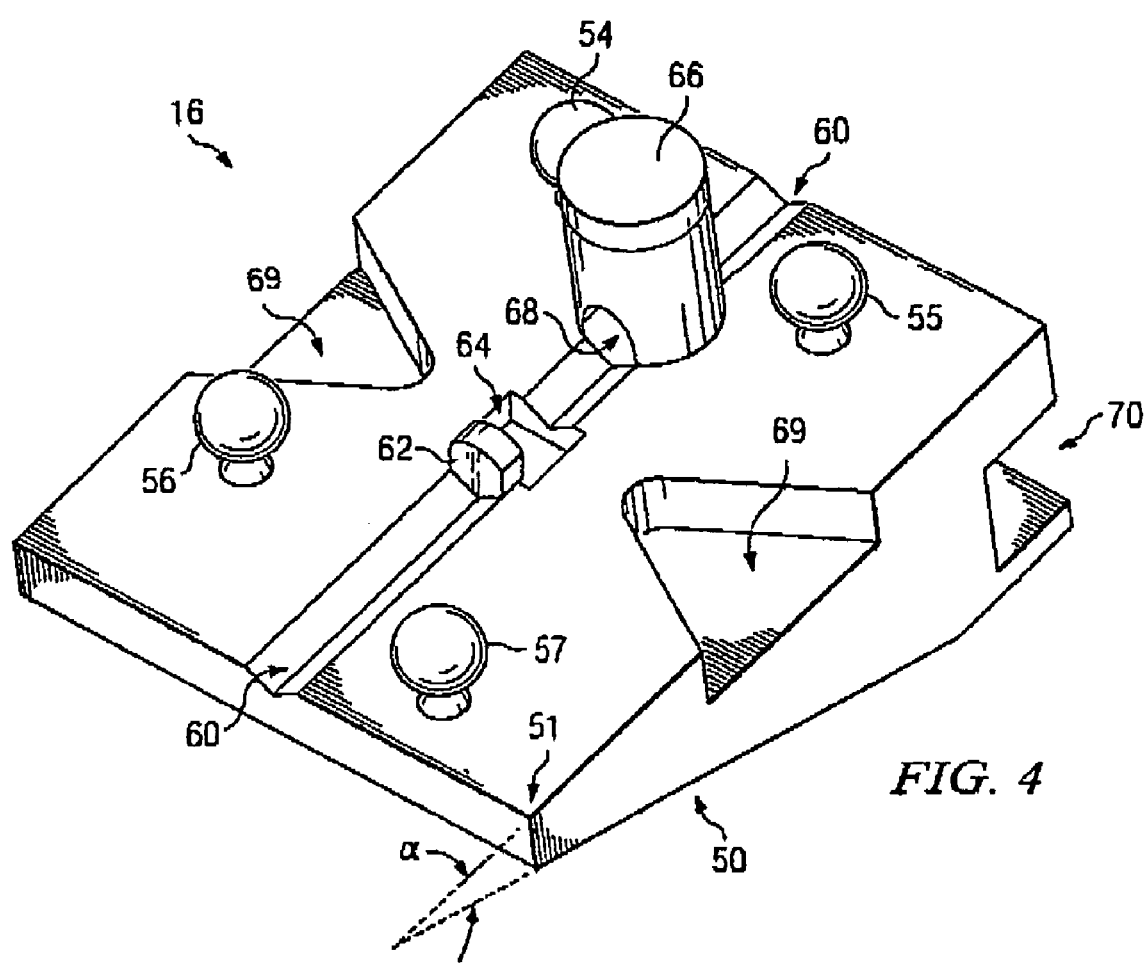
FIG. 4 is a perspective view of an exemplary embodiment of a tool calibrator.

FIG. 4 is a more detailed perspective view of tool calibrator 16 of the present invention. Tool calibrator 16 includes a base 50 and a top surface 51. Top surface 51 lies in a plane that is at an acute angle, α, relative to the plane formed by base 50. The inclined top surface allows the user to better present the tool to cameras 24 during calibration for improved detection. A plurality of position indicating elements 54–57 are secured in a fixed known and spaced relationship with one another to top surface 51. Position indicating elements 54–57 may be passive or active and are detectable by cameras 24 of locating system 22 to provide location and orientation information to image guided medical system 14. A groove or channel 60 in the shape of a V is fanned into top surface 51 running substantially the entire length of tool calibrator 16. A stop 62 is formed at a known and fixed location to allow the tip of a tool (not shown in this view) inserted into V-groove 60 to rest against stop 62. A wider and deeper expansion slot 64 is formed in groove 60 immediately prior to tool stop 62. Slot 64 can accommodate tool tips that have a larger diameter or than the body of the tool or with an irregular shape to still allow the tool to rest snuggly in V-groove 60. The locations of V-groove 60 and stop 62 relative to position indicating elements 54–57 are provided to or stored in image guided surgery system 14 to be used during calibration. A self-actuating tool holder 66 is positioned above V-groove 60 to securely hold the tool in the groove. Self-actuating tool holder 66 may be a spring biased ball clamp, which operates with lever action to allow the tool to slide underneath and past a ball spring 68 without requiring the user to adjust or open the clamp with a second hand. Ball spring 68 is typically constructed from a ball bearing having a smooth surface and biased by a spring housed in a cylindrical chamber in self-adjustable tool holder 66. Preferably, self-actuating tool holder 66 is positioned substantially mid-point between stop 62 and the end of V-groove 60, so that the force of the ball-spring is operable to hold the tool securely in place. To make tool calibrator 16 lighter in weight, several cutouts or cavities 69 and 70 are formed in the body of the tool calibrator without influencing the overall integrity of tool calibrator.

Figure 5:
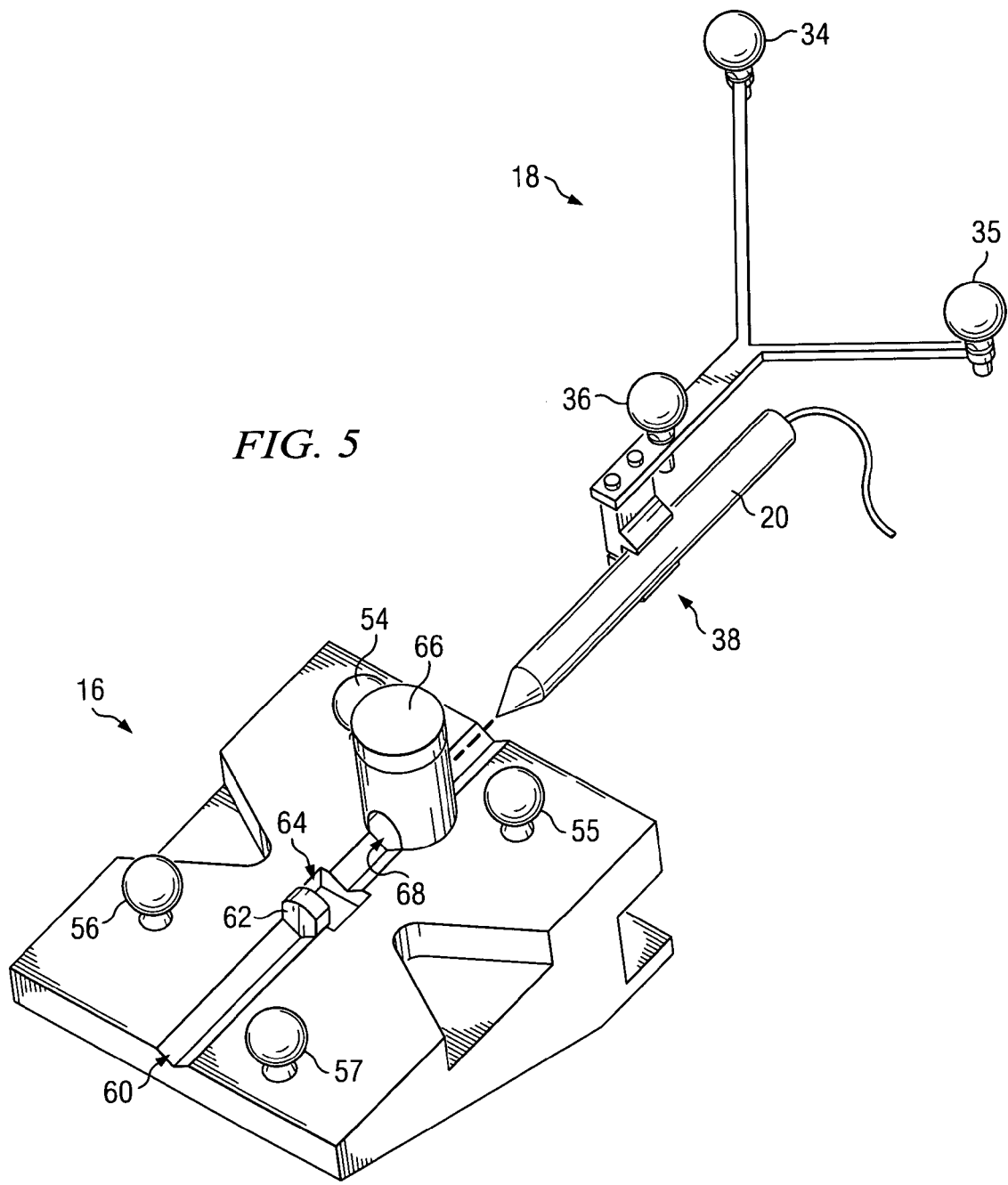
FIG. 5 is a perspective view of the tool tracker and tool calibrator.

FIG. 5 is a perspective view of tool tracker 18 holding tool 20 in alignment with tool calibrator 16. Tool 20 is held by clamp 38 of tool tracker 18 for inserting tool 20 into tool calibrator 16 along V-groove 60 until the tip of the tool comes to a stop against stop 62. Self-actuating tool holder 66 guides and holds tool 20 snuggly against the sides of V-groove 60.

To register the axis of tool 20, the user situates tool calibrator 16, tool tracker 18 and tool 20 such that all position indicating elements 34–36 and 54–57 are detectable by cameras 24 (FIG. 1). The user then enters a predetermined command into image guided surgery system 14 to initiate the calibration process. The user then rotates tool tracker 18 and tool 20 first in one direction than in the other direction. In one embodiment, tool tracker 18 and tool 20 are first rotated at least 60 degrees in one direction, and then 120 degrees in the other direction. Ball spring 68 allows tool 20 to roll smoothly in place while being rotated to reduce potential registration errors. The tool rotation allows cameras 24 to capture and relay the location of position indicating elements 34–36 as the tool is rotated to image guided surgery system 14. From the position information, the longitudinal axis of tool 20 in space can be triangulated and determined. Furthermore, because the tip of tool 20 is at a known location due to the capture and relay of the location of position indicating elements 54–57, the spatial relationship of the tool tip to tool tracker position indicating elements 34–36 can also be determined. After calibration, tool 20 can be withdrawn from tool calibrator 16, but its position and orientation may be continually tracked by capturing the position and orientation of tool tracker position indicating elements 34–36 by the tracking system of image guided system 14. As a result, the position of the tool axis and tool tip are known to image guided system by tracking the position of elements 34–36.

Unlike some conventional systems, the tool tracker and tool calibrator system of the present invention can be used with any tool with general dimensions not more than specified size limits. The use of C-clamp 38, self-actuating clamp 66 and expansion slot 64 accepts tools with a wide variety of sizes and geometries. The present invention does not require the use of special medical tools that has built-in position comprising markers. Since the tool registration process is not dependent on determining an actual tool diameter as in conventional systems, any tool with a generally symmetrical geometry may be used. Another advantage of the present invention is that a surgeon or assistant can position the tool in tool calibrator 16 without using a second hand to hold the calibrator or operate any clamp to hold the tool in the calibrator. Only one hand holding the tool and tool tracker is needed to situate the tool. The angled top surface of the tool calibrator further provides the advantage of a greater line-of-sight presentation to the cameras to capture and record the location and orientation of the position comprising elements on the tool calibrator. As described herein, the tool tracker and tool calibrator have simple shapes and simple construction, which allow them to be more easily and economically manufactured.

It will be understood by those skilled in the art that various changes, alterations, modifications, mutations and derivations in form and detail may be made to the forgoing examples without departing from the scope of the invention as set out in the appended claims.

What is claimed is:

1. A method of calibrating a medical or surgical tool to a tracking system, comprising:
    attaching to the tool a plurality of position indicating elements having a predetermined spatial relationship with one another;
    placing the tool onto a support frame of a tool calibrator adapted for permitting rotation of the tool about an axis;
    detecting with a tracking system the positions of the plurality of position indicating elements while the tool is being rotated; and
    determining a position of the axis of the tool relative to the plurality of position indicating elements based on the detected positions of the plurality of position indicating elements while the tool is being rotated.

2. The method, as set forth in claim 1, wherein the tool is rotated first in one direction and then in an opposite direction.

3. The method, as set forth in claim 1, wherein the support includes a tool stop, wherein placing the tool onto the support frame includes placing a tip of the tool adjacent the tool stop, and wherein the method further includes determining a position of the tip of the tool relative to the plurality of position indicating elements based on a known location of the tool stop.

4. The method, as set forth in claim 3, wherein the known location of the tool stop is derived from determining with the tracking system positions of a second plurality of position indicating elements having a known spatial relationship to the tool stop.

5. The method, as set forth in claim 1, wherein the support frame includes a groove formed in a surface of the tool calibrator.

6. The method, as set forth in claim 5, wherein the groove is substantially "V" shaped.

7. The method, as set forth in claim 6, wherein placing the tool onto the support frame comprises sliding the tool along the groove and under a self-actuating ball spring clamp operable to retain the tool snuggly in the groove.

8. A system for calibrating an orientation of an axis and a location of a tip of a medical or surgical tool to position locating elements affixed to the tool, the system comprising:
   a support surface;
   a groove disposed in the support surface for rotatably receiving the tool;
   a stop member disposed in the groove to retain the tip of the tool;
   a first plurality of position indicating elements disposed on the support surface, the position indicating elements having fixed and known spatial relationships with one another and to the stop member;
   a tool tracker including a second plurality of position indicating elements fixed in spatial relationships with one another, the tool tracker operable to be secured to the tool; and
   a computer programmed to determine an axis of rotation of the tool when the tool tracker is secured to the tool based on locations of the second plurality of position indicating elements as the tool is rotated in the groove.

9. The system, as set forth in claim 8, wherein the support surface is planar.

10. The system, as set forth in claim 8, wherein the first plurality of position indicating elements comprise at least three energy reflectors secured to the support surface.

11. The system, as set forth in claim 8, wherein the support surface contains a tool holder operable to retain the tool on the support surface.

12. The system, as set forth in claim 11, wherein the tool holder includes a self-actuating ball spring clamp.

13. A method of registering a tool to an image guided system, comprising:
   attaching to the tool a first plurality of position indicating elements having a predetermined spatial relationship with one another;
   placing the tool onto a support of a tool calibrator operable to permit rotation of the tool about a known axis, the tool calibrator having a second plurality of position indicating elements secured thereto;
   rotating the tool on the support;
   detecting positions of the first plurality of position indicating elements and of the second plurality of position indicating elements while the tool is being rotated; and
   registering a tool tip and a tool longitudinal axis spatial location relative to the detected locations of the first and second plurality of position indicating elements.

14. The method, as set forth in claim 13, wherein placing the tool comprises sliding the tool along a groove and under a self-actuating ball spring clamp operable to retain the tool snuggly in the groove.

15. The method, as set forth in claim 13, wherein placing the tool comprises sliding the tool along a groove until the tool tip comes to rest against a tool stop.

16. A system for calibrating an orientation of an axis and a location of a tip of a medical or surgical tool to position locating elements affixed to the tool, the system comprising:
   a support surface;
   a groove disposed in the support surface for rotatably receiving the tool;
   a stop member disposed in the groove to retain the tip of the tool;
   a plurality of position indicating elements disposed on the support surface, the position indicating elements having fixed and known spatial relationships with one another and to the tool stop member; and
   an image guided surgery system programmed to determine an axis of rotation of the tool based on locations of the position locating elements affixed to the tool as the tool is rotated in the groove.

* * * * *